United States Patent [19]
Yoon

[11] Patent Number: 5,389,080
[45] Date of Patent: Feb. 14, 1995

[54] ENDOSCOPIC PORTAL FOR USE IN ENDOSCOPIC PROCEDURES AND METHODS THEREFOR

[76] Inventor: InBae Yoon, 2101 Highland Ridge Dr., Phoenix, Md. 21131

[21] Appl. No.: 40,560

[22] Filed: Mar. 31, 1993

Related U.S. Application Data

[63] Continuation-in-part of Ser. No. 557,869, Jul. 26, 1990.

[51] Int. Cl.⁶ .............................................. A61M 5/00
[52] U.S. Cl. ...................... 604/167; 604/169
[58] Field of Search ...................... 604/167, 169, 256

[56] References Cited

U.S. PATENT DOCUMENTS

| | | |
|---|---|---|
| 3,044,461 | 7/1962 | Murdock . |
| 3,509,883 | 5/1970 | Dibelius . |
| 3,747,812 | 7/1973 | Karman et al. . |
| 3,788,318 | 1/1974 | Kim et al. . |
| 3,789,852 | 2/1974 | Kim et al. . |
| 3,833,003 | 9/1974 | Taricco . |
| 3,895,632 | 7/1975 | Plowiecki . |
| 3,994,287 | 11/1976 | Turp et al. . |
| 4,177,814 | 12/1979 | Knepshield et al. . |
| 4,187,849 | 2/1980 | Stim . |
| 4,240,411 | 12/1980 | Hosono . |
| 4,379,458 | 4/1983 | Bauer et al. . |
| 4,475,548 | 10/1984 | Muto ........................ 128/912 |
| 4,524,770 | 6/1985 | Orandi . |
| 4,535,773 | 8/1985 | Yoon . |
| 4,601,710 | 7/1986 | Moll . |
| 4,654,030 | 3/1987 | Moll et al. . |
| 4,655,752 | 4/1987 | Honkanen et al. . |
| 4,668,221 | 5/1987 | Luther . |
| 4,735,614 | 4/1988 | Yapp et al. . |
| 4,769,005 | 9/1988 | Ginsburg et al. . |
| 4,790,817 | 12/1988 | Luther . |
| 4,808,168 | 2/1989 | Warring . |
| 4,899,729 | 2/1990 | Gill et al. . |
| 4,902,280 | 2/1990 | Lander . |
| 4,919,653 | 4/1990 | Martinez et al. . |
| 4,931,042 | 6/1990 | Holmes et al. . |
| 4,943,280 | 7/1990 | Lander . |
| 5,002,557 | 3/1991 | Hasson . |
| 5,030,206 | 7/1991 | Lander . |
| 5,053,016 | 10/1991 | Lander . |
| 5,066,288 | 11/1991 | Deniega et al. . |
| 5,104,383 | 4/1992 | Shichman . |
| 5,104,389 | 4/1992 | Deem et al. ................. 604/167 |
| 5,112,321 | 5/1992 | Hiltebrandt . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,129,885 | 7/1992 | Green et al. . |
| 5,139,511 | 8/1992 | Gill et al. . |
| 5,141,498 | 8/1992 | Christian . |
| 5,158,553 | 10/1992 | Berry et al. ................. 604/256 |
| 5,167,636 | 12/1992 | Clement . |

(List continued on next page.)

FOREIGN PATENT DOCUMENTS 1024410 3/1966 United Kingdom .

*Primary Examiner*—Paul J. Hirch

[57] ABSTRACT

An endoscopic portal includes a portal sleeve for insertion through a cavity wall and having an open distal end for positioning within the cavity and an open proximal end for positioning externally of the cavity and a valve assembly disposed adjacent the portal sleeve proximal end. The valve assembly includes a bladder having a passage therethrough permitting insertion of instruments of various sizes in the portal sleeve through the passage of the bladder. The bladder has means therein for compressing the passage to cause the bladder to contact the instruments inserted through the passage in sealing relation. The portal sleeve includes an expandable lumen allowing instruments and objects larger in size than the inner diameter of the portal sleeve to be passed therethrough. A method of inserting instruments through an endoscopic portal includes the steps of inserting an instrument through a passage of a bladder filled with compressible material adjacent an end of the endoscopic portal disposed externally of an anatomical cavity and compressing the passage with the compressible material to cause the bladder to contact the instrument in sealing relation to prevent undesired fluid flow through the endoscopic portal.

30 Claims, 9 Drawing Sheets

U.S. PATENT DOCUMENTS

| | | |
|---|---|---|
| 5,176,648 | 1/1993 | Holmes et al. . |
| 5,176,651 | 1/1993 | Allgood et al. . |
| 5,176,697 | 1/1993 | Hasson et al. . |
| 5,180,373 | 1/1993 | Green et al. . |
| 5,183,464 | 2/1993 | Dubrul et al. . |
| 5,188,607 | 2/1993 | Wu ................................. 604/169 |
| 5,197,955 | 3/1993 | Stephens et al. . |
| 5,201,714 | 4/1993 | Gentelia et al. . |
| 5,207,656 | 5/1993 | Kranys . |
| 5,209,736 | 5/1993 | Stephens et al. . |
| 5,211,633 | 5/1993 | Stouder, Jr. . |
| 5,256,150 | 10/1993 | Quiachun et al. ................ 604/167 |

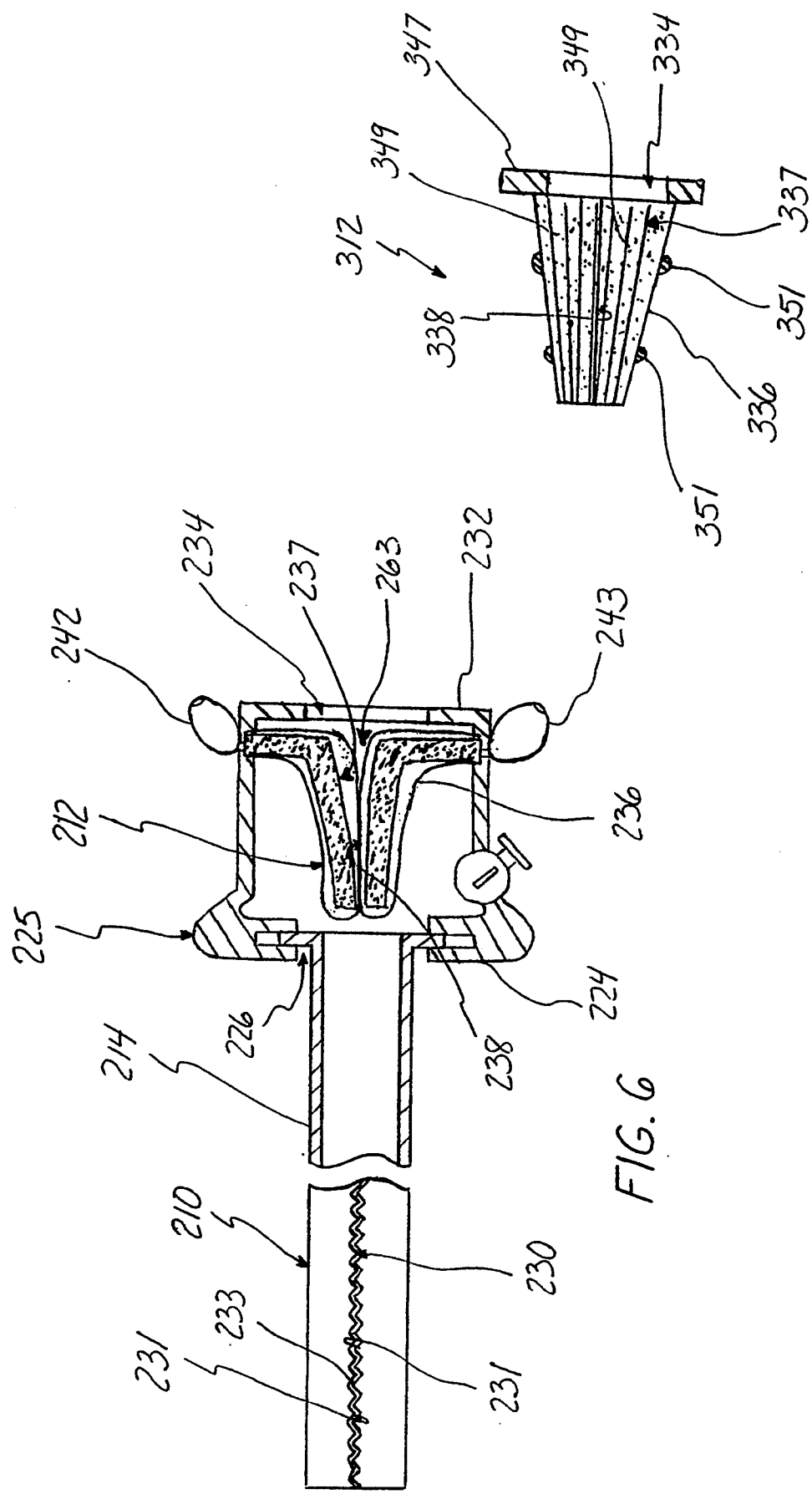

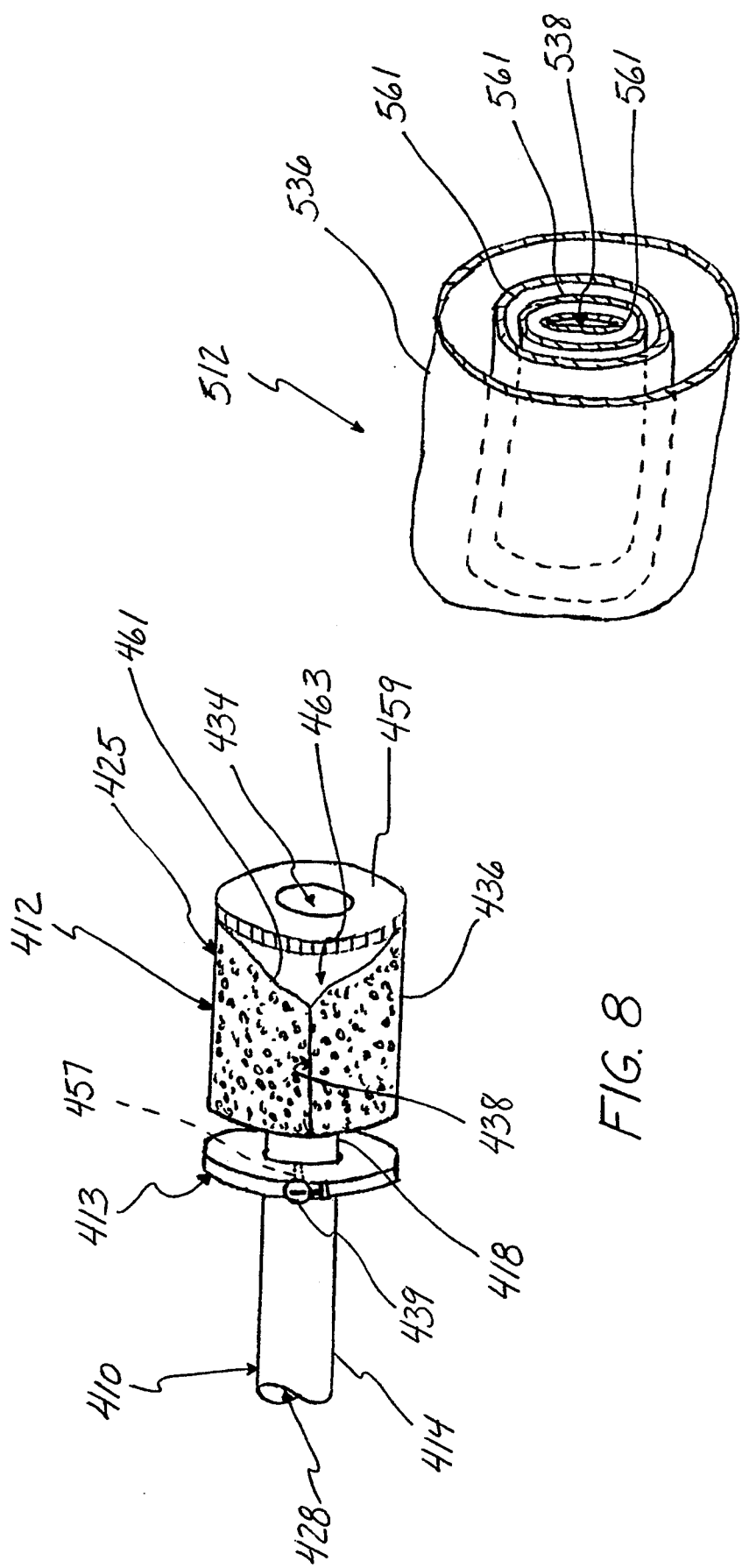

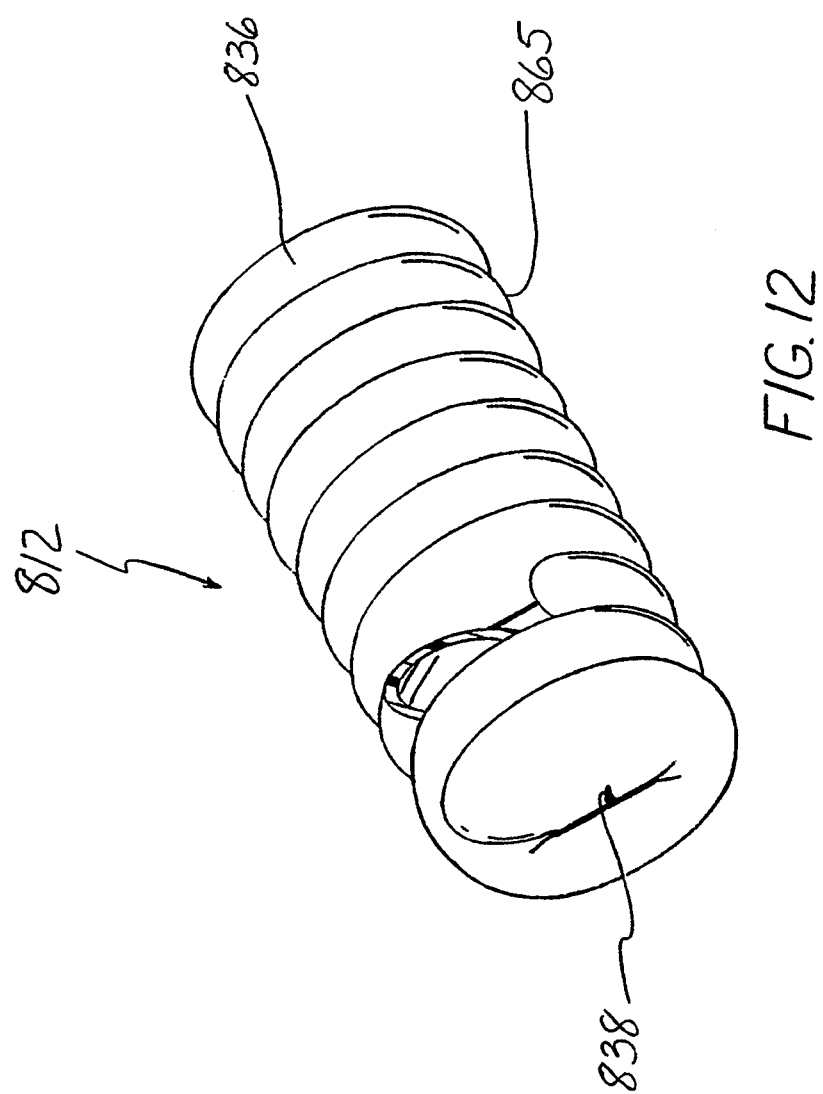

ENDOSCOPIC PORTAL FOR USE IN ENDOSCOPIC PROCEDURES AND METHODS THEREFOR

This is application is a continuation-in-part of pending patent application Ser. No 07/577,869 filed Jul. 26, 1990, which is incorporated herein by reference.

BACKGROUND OF THE INVENTION

1. Field of the Invention

The present invention pertains to instruments and methods for use in endoscopic procedures and, more particularly, to an endoscopic portal providing a variable size passage to a surgical site within an anatomical cavity to prevent undesired fluid flow through the portal while allowing surgical instruments of various sizes to be selectively introduced through the portal and to permit expansion of the portal to facilitate removal of objects from and insertion of objects in the anatomical cavity as well as methods therefor.

2. Description of the Prior Art

Surgical procedures involving the placement of an endoscopic portal, such as a sleeve or cannula, through a wall of an anatomical cavity to provide a passage for insertion of surgical instruments into the cavity frequently require that the passage be sealed to prevent undesired flow of fluids through the endoscopic portal. For example, in many endoscopic medical procedures access to the interior of an anatomical cavity is gained by utilizing a surgical penetrating instrument, such as a trocar, obturator or needle, having a sharp penetrating point for penetrating a wall of the cavity to establish communication with the interior thereof. Upon penetration of the cavity wall by the penetrating instrument, a sleeve or cannula is left in place for utilization as a portal to introduce surgical instruments into the anatomical cavity. The surgical penetrating instrument is usually received within the sleeve, which passes through the wall of the anatomical cavity with the penetrating instrument and remains in situ after withdrawal of the penetrating instrument therefrom to provide a lumen establishing communication with a surgical site in the interior of the cavity. The sleeve typically has a proximal end disposed externally of the anatomical cavity and secured in a housing provided with a valve that allows the penetrating instrument to be inserted into and removed from the sleeve. Once the penetrating instrument has been removed from the sleeve, various instruments can be introduced into the anatomical cavity via the lumen of the sleeve dependent upon the operative procedure to be performed.

It is extremely important in endoscopic procedures to prevent undesired fluid flow to and from the surgical site; and, accordingly, the portal must be sealed prior to and subsequent to the introduction of surgical instruments and while such instruments are in place. In addition, fluids, such as gaseous phase carbon dioxide or nitrous oxide, may be introduced into the anatomical cavity for insufflation as part of the endoscopic procedure, and the escape of such fluids must be prevented during penetration of the cavity as well as during the operative procedure. The valves of endoscopic portals typically have a valve passage with a size corresponding to an outer diameter or size of the penetrating instrument to form a seal with the penetrating instrument, the size of the penetrating instrument varying in accordance with the endoscopic procedure being performed and the type of anatomical cavity being penetrated. Furthermore, the valves of endoscopic portals typically have been designed to close when the penetrating instrument is removed to prevent the flow of fluids through the valves. Many prior art endoscopic portals utilize a flapper or gate valve that is normally biased to a closed position and movable to an open position to allow the penetrating instrument to be inserted through the valve passage, which has a single, predetermined size corresponding to the size of the penetrating instrument. However, additional instruments to be introduced into the anatomical cavity through the valve passage may be of diverse types and sizes, and it will be appreciated that fluid can escape past smaller size instruments. Accordingly, such endoscopic portals suffer from the disadvantages of allowing the passage or leakage of fluids when surgical instruments smaller in size than the size of the single valve passage are introduced therethrough or of limiting the instruments to be introduced through the portal to a single size. Many attempts have been made to variably seal endoscopic portals to allow the introduction of various sized instruments therethrough; however, there still exists a great need for an endoscopic portal having a universal valve to prevent the escape of fluid from an anatomical cavity by sealing variably sized instruments passing through the portal without requiring placement in the portal of seals of various sizes.

SUMMARY OF THE INVENTION

Accordingly, it is a primary object of the present invention to overcome the above described disadvantages of prior art endoscopic portals.

Another object of the present invention is to prevent undesired fluid flow through an endoscopic portal while allowing introduction of instruments of various sizes therethrough via a passage of a valve assembly having means for compressing the passage to cause the valve assembly to sealingly contact the instruments.

A further object of the present invention is to provide a valve assembly for an endoscopic portal to prevent undesired fluid flow through the endoscopic portal while allowing instruments of various sizes to be inserted therethrough, the valve assembly including a bladder filled with a material to cause the bladder to sealingly contact the instruments extending through a passage of the bladder.

Still another object of the present invention is to provide a valve assembly for an endoscopic portal to normally seal the endoscopic portal to prevent undesired fluid flow therethrough and to open a single passage through the valve assembly to variable sizes corresponding to the sizes of instruments to be passed therethrough in sealing relation with the valve assembly.

The present invention has as a further object to provide a valve assembly for an endoscopic portal, the valve assembly including means for causing a passage of the valve assembly to conform to the size of instruments extending therethrough in sealing relation.

An additional object of the present invention is to provide an endoscopic portal including a sleeve or cannula having an expandable lumen in combination with a valve assembly having an expandable passage therethrough to allow objects of increased size to pass through the sleeve and/or the valve.

Yet a further object of the present invention is to provide a method of inserting instruments through an endoscopic portal in endoscopic procedures including the steps of inserting an instrument through a passage of a valve assembly of the endoscopic portal and compressing the passage to cause the valve assembly to contact the instrument in sealing relation.

Some of the advantages of the present invention over the prior art are that various endoscopic procedures can be performed with a single portal, thusly reducing instrument cost and the time required to complete endoscopic procedures, a single endoscopic portal can be used with various sizes and types of instruments without requiring manipulation of the endoscopic portal or the addition or interchanging of different sized seals, and the endoscopic portal can be inexpensively manufactured to be economically disposable for single patient use.

The present invention is generally characterized in an endoscopic portal for establishing communication with an anatomical cavity through a wall of the cavity including an elongate tubular portal sleeve having an open distal end for positioning within the cavity and an open proximal end for positioning externally of the cavity with the portal sleeve inserted through the cavity wall and a valve assembly disposed adjacent the portal sleeve proximal end for preventing undesired passage of fluid through the portal sleeve. The valve assembly includes a passage therethrough for permitting instruments to be inserted in and removed from the lumen of the portal sleeve via the passage. The valve assembly has means, including a compressible material or spine member, for causing the valve assembly to sealingly contact instruments of various sizes inserted through the passage and to close the passage when the instruments are removed to prevent the undesired flow of fluids through the portal sleeve. The portal sleeve includes an expandable lumen for receiving instruments or objects larger than the inner diameter of the portal sleeve. A method of inserting instruments through an endoscopic portal according to the present invention includes the steps of inserting an instrument through a passage of a valve assembly of the endoscopic portal and compressing the passage to cause the valve assembly to sealingly contact the instruments and thusly prevent undesired fluid flow through the endoscopic portal.

Other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 6 is a side view, partly in section, of another modification of the endoscopic portal according to the present invention.

FIG. 7 is a side sectional view of a modification of the valve assembly for the endoscopic portal according to the present invention.

FIG. 8 is a side view, partly in section, of a further modification of the endoscopic portal according to the present invention.

FIG. 9 is a perspective sectional view of a modification of the valve assembly for the endoscopic portal according to the present invention.

FIG. 12 is a perspective view, partly in section, of another modification of the valve assembly for the endoscopic portal according to the present invention.

DESCRIPTION OF THE PREFERRED EMBODIMENTS

Figure 1:
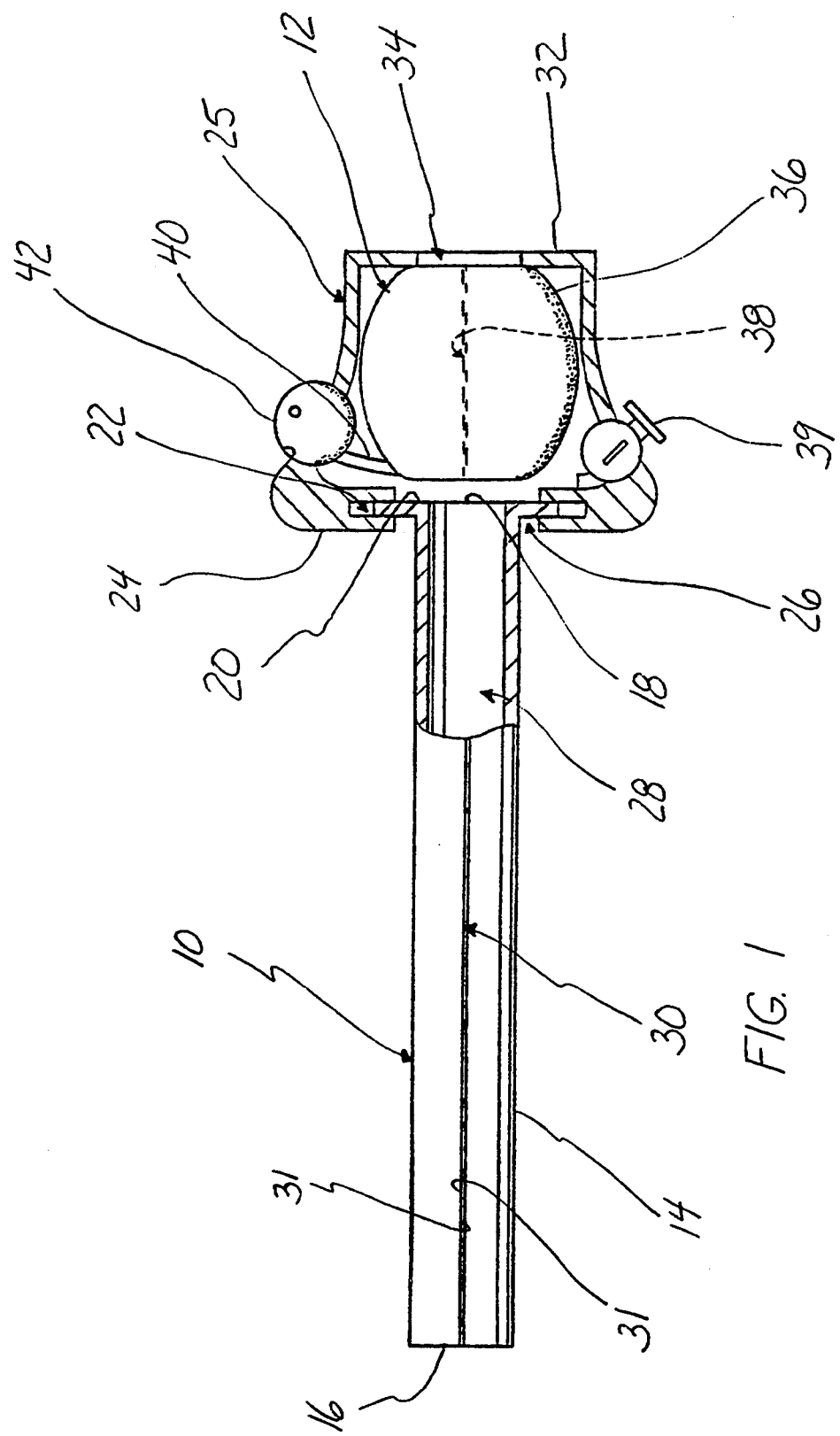
FIG. 1 is a side view, partly in section, of an endoscopic portal according to the present invention.

An endoscopic portal 10 including a valve assembly 12 according to the present invention is illustrated in FIG. 1. Endoscopic portal 10 includes an elongate tubular or cylindrical portal sleeve or cannula 14 for being positioned through a wall of an anatomical cavity during puncturing or penetration of the cavity wall by a penetrating instrument to provide access to an operative site within the cavity. Sleeve 14 has an open distal end 16 for being disposed within the anatomical cavity and an open proximal end 18 for being disposed externally of the cavity with the sleeve inserted through the cavity wall. Distal end 16 preferably has a blunt configuration to prevent damage to tissue and organ structure within the anatomical cavity and can be non-tapered as shown in FIG. 1 or tapered, such as conically tapered. Sleeve 14 terminates proximally at a flange 20 at proximal end 18, the flange 20 being received in a recess 22 in a forward wall 24 of a housing 25 mounting the sleeve 14. Flange 20 and recess 22 can have various configurations including annular configurations as shown in FIG. 1 with the flange 20 having an outer diameter smaller than the diameter of recess 22 to permit diametric or lateral outward expansion of portal 10 as will be explained further below. In addition to the flange and recess shown, sleeve 14 can be permanently or removably coupled to housing 25 in many various ways while allowing diametric or outward expansion of portal 10. Forward wall 24 has an annular aperture 26 therein allowing passage therethrough by sleeve 14, and the aperture 26 has a diameter larger than the outer diameter of sleeve 14 to permit diametric expansion thereof. It will be appreciated that flange 20, recess 22 and aperture 26 can have various configurations with the peripheries of flange 20 and sleeve 14 being disposed within the peripheries of recess 22 and aperture 26, respectively, to permit expansion of portal 10. It will be further appreciated that the sizes of flange 20, recess 22 and aperture 26 can be varied in accordance with the amount of expansion desired for portal 10 and that by increasing the gaps or spaces between the peripheries of flange 20 and sleeve 14, and the peripheries of recess 22 and aperture 26, respectively, greater expansion of portal 10 can be permitted. Where it is desired to limit or control the amount of expansion for portal 10, flange 20, recess 22 and aperture 26 can be sized such that the periphery of flange 20 or sleeve 14 or both contacting the material of forward wall 24 serves as a positive stop or abutment limiting diametric expansion of portal 10.

Portal 10 can be made of a medical grade material such as metal or plastic or a flexible, expandable or stretchable material such as rubber permitting sleeve 14 to be normally disposed in a closed, non-flexed, non-expanded or non-stretched state illustrated in FIG. 1 and allowing lumen 28 to be diametrically or laterally expanded or moved in a direction transverse to a longitudinal axis of the sleeve to an open, flexed, expanded or stretched state to increase the diameter or cross-sectional size of lumen 28 to accommodate instruments or objects therein larger than the diameter or cross-sectional size of lumen 28 in the closed state. Depending on the material utilized for portal 10, a longitudinal slit 30 can be provided through the thickness of the wall of sleeve 14 to extend the entire length thereof to facilitate flexing, expansion or stretching of the portal 10. Slit 30 defines opposing edges 31 that touch or are adjacent or substantially adjacent one another in the closed state and are disposed further apart from one another in the open state.

Housing 25 can be made of any suitable material, such as plastic, and can have various configurations including a cylindrical configuration as illustrated in FIG. 1 with a flared forward end to facilitate grasping by a surgeon. Housing 25 has a rear wall 32 with an opening 34 therein longitudinally aligned with lumen 28 to allow various instruments to be inserted through portal 10 via the housing. Opening 34 has a diameter or peripheral size larger than the diameter of lumen 28 to accommodate instruments or objects larger in size than the lumen diameter in the closed state.

Valve assembly 12 includes a bladder 36 disposed in housing 25, the bladder having a longitudinal passage 38 therethrough aligned with lumen 28 and opening 34. Bladder 36 can be made of any suitable expandable material to form an envelope for holding or containing a compressible material supplied to the interior thereof. At least the portion of the bladder 36 defining passage 38 is made of a strong, non-tearing or tearing resistant, expandable, medical grade membrane, such as Tecoflex EG-85A manufactured by Thermedics, Inc., Teflon, Goretex or rubber, allowing instruments or objects to pass or slide easily therethrough. For increased strength and ease of insertion of instruments, the passage defining portion of the bladder and, in particular, the area of entry for instruments to be inserted in passage 38, can be formed of multiple layers of the expandable membrane. Bladder 36 can be made unitarily, integrally as one piece or as multiple pieces joined together by any suitable means to prevent leakage or escape of compressible material therefrom. The interior of bladder 36 can be made up of a single compartment or a plurality of compartments where the bladder has inner walls or partitions. The bladder 36 can be sized and shaped to have various predetermined sizes and configurations in an expanded state when supplied or filled with a compressible material as explained further below including spherical, partial spherical, heart-shaped, toroidal or donut-shaped, disk-shaped, funnel-shaped, conical or nipple-shaped configurations, for example. The size and configuration of bladder 36 when supplied with compressible material can be selected such that the open proximal end 18 of sleeve 14 remains unsealed allowing fluid, such as insufflation gas, to be supplied to the anatomical cavity through the lumen 28. A stopcock 39 or other valve communicating with the interior of housing 25 can be provided for supplying fluids to the anatomical cavity via lumen 28. The stopcock 39 or other device can be mounted on housing 25 in many various ways, such as adjacent forward wall 24 to facilitate operation by the hand of the surgeon grasping housing 25 as shown in FIG. 1.

Bladder 36 is connectable to a source or supply of compressible material, such as air. Various devices including various valves can be used to supply air to the interior of bladder 36; and, as shown in FIG. 1, a tube 40 joined to a squeeze bulb 42 is connected with bladder 36 to communicate with the interior thereof for supplying air to inflate or expand the bladder. When filled with compressible material, bladder 36 is in the expanded state with the bladder assuming an expanded configuration of increased size or volume to close or compress passage 38 due to the pressure of the compressible material while being temporarily contractable or deformable to open passage 38 in response to pressure applied externally to the bladder. Accordingly, what is meant by a compressible material is a material for maintaining the shape, size or configuration of bladder 36 in the expanded state while allowing temporary deformation or contraction of the expanded configuration in response to external pressure applied to the bladder. The device utilized to supply air to bladder 36 can be integral with or separate from housing 25; and, as illustrated in FIG. 1, squeeze bulb 42 extends partly through a wall of housing 25 for operation by the hand of the surgeon grasping housing 25. The same device can be utilized to supply air to bladder 36 for expansion and to remove or release air therefrom, or separate devices including various valves and squeeze bulbs can be provided for supplying air to and removing air from the bladder. The bladder 36 can be normally empty in a non-expanded or contracted state prior to being inflated, or the bladder can be partially pre-filled with compressible material, including air, saline, gel, foam or sponge, for example, which remains within the bladder as a spine providing some shape in the contracted state and guiding the bladder to close passage 38. Where the bladder 36 is partially filled with a compressible material in the contracted state, the compressible material can be disposed in a separate interior compartment of the bladder.

According to a method of operation for the endoscopic portal 10 and valve assembly 12 according to the present invention, bladder 36 can normally be supplied in the non-expanded or contracted state with the interior of the bladder empty or partially filled with a compressible material. When it is desired to utilize the endoscopic portal 10 in an endoscopic operative procedure, housing 25 is grasped by the hand of a surgeon, and squeeze bulb 42 is pressed or squeezed with the fingers of the same hand to supply air to the bladder interior. The air supplied to bladder 36 causes the bladder 36 to assume a configuration in the expanded state of increased volume or size with passage 38 closed, compressed or collapsed in a direction transverse to a longitudinal axis of the passage to form a seal along the length of the passage preventing fluid flow through the valve assembly 12 as shown in FIG. 1, it being noted that passage 38 in FIG. 1 is illustrated as being slightly open for the sake of clarity in identifying the passage. Depending on the configuration of bladder 36 in the expanded state, opening 34 can be covered by the bladder as shown in FIG. 1 to form a seal at the opening, or the opening can be uncovered with a seal provided through the valve assembly due to closing of passage 38. Proximal end 18 of sleeve 14 can remain uncovered by the bladder to allow fluid to be supplied to or withdrawn from an anatomical cavity via stopcock 39. A penetrating instrument, such as a trocar, obturator or needle, having a sharp tip for penetrating a wall of an anatomical cavity is inserted through the passage 38 to be received within sleeve 14 as described in applicant's co-pending patent application Ser. No. 07/577,869 filed Jul. 26, 1990, the specification of which is incorporated herein by reference. Insertion of the penetrating instrument in passage 38 applies external pressure to bladder 36 causing the material within the bladder to be compressed and temporarily deforming the bladder to open passage 38 to receive the penetrating instrument. Where a device is provided for removing air, air can be removed from the bladder 36 if needed to reduce the force required to open passage 38. With the penetrating instrument extending through passage 38, bladder 36 conforms to the size and configuration of the instrument along passage 38 to be in sealing relation or contact with the penetrating instrument to form a seal therewith along the length of the passage preventing the flow of fluid through valve assembly 12. If desired, the penetrating instrument can be inserted through valve assembly 12 prior to inflation of bladder 36 and the bladder inflated following insertion of the penetrating instrument through passage 38. It will be appreciated that various sizes of penetrating instruments can be utilized with the endoscopic portal in that the single passage 38 will open to a size just large enough to receive the penetrating instrument with bladder 36 forming a seal therewith. Where a penetrating instrument having a diameter larger than the diameter of lumen 28 is utilized, sleeve 14 will be expanded diametrically or laterally outwardly by the penetrating instrument from the closed state wherein edges 31 touch or are separated from one another by a minimal gap to the open state wherein the edges are separated or the gap increased to expand lumen 28 to a size large enough to receive the penetrating instrument. The penetrating instrument can now be utilized to penetrate a wall of an anatomical cavity with the sleeve 14 passing through the cavity wall during penetration to position distal end 16 within the anatomical cavity while proximal end 18 remains externally of the cavity. During penetration and while the penetrating instrument is in place, fluid flow to and from the cavity through valve assembly 12 is prevented due to the seal formed by bladder 36 with the penetrating instrument. Where stopcock 39 is provided, fluid can be supplied to the anatomical cavity, and such fluid cannot escape through valve assembly 12. Once distal end 16 of sleeve 14 is within the anatomical cavity, the penetrating instrument can be withdrawn from the endoscopic portal 10 leaving the endoscopic portal in place. Upon removal of the penetrating instrument, bladder 36 returns to its expanded state configuration due to the pressure of the compressible material to cause passage 38 to automatically close and thusly seal endoscopic portal 10. Instruments of various sizes can be inserted in the anatomical cavity through the lumen 28 of the endoscopic portal with bladder 36 deforming or contracting in response to external pressure applied by the instruments to open passage 38 to a size and shape to receive the instruments with bladder 36 forming a seal therewith. Instruments larger in size than the diameter of lumen 28 can be inserted at the anatomical cavity, and tissue and other objects larger in size than the diameter of lumen 28 can be removed from the anatomical cavity due to diametric or lateral expansion of sleeve 14. It will be appreciated that air can be selectively removed from bladder 36 to control or limit the external size of the bladder when inserting and removing larger instruments or objects through the valve assembly such that the size of housing 25 can be minimized.

Figure 2:
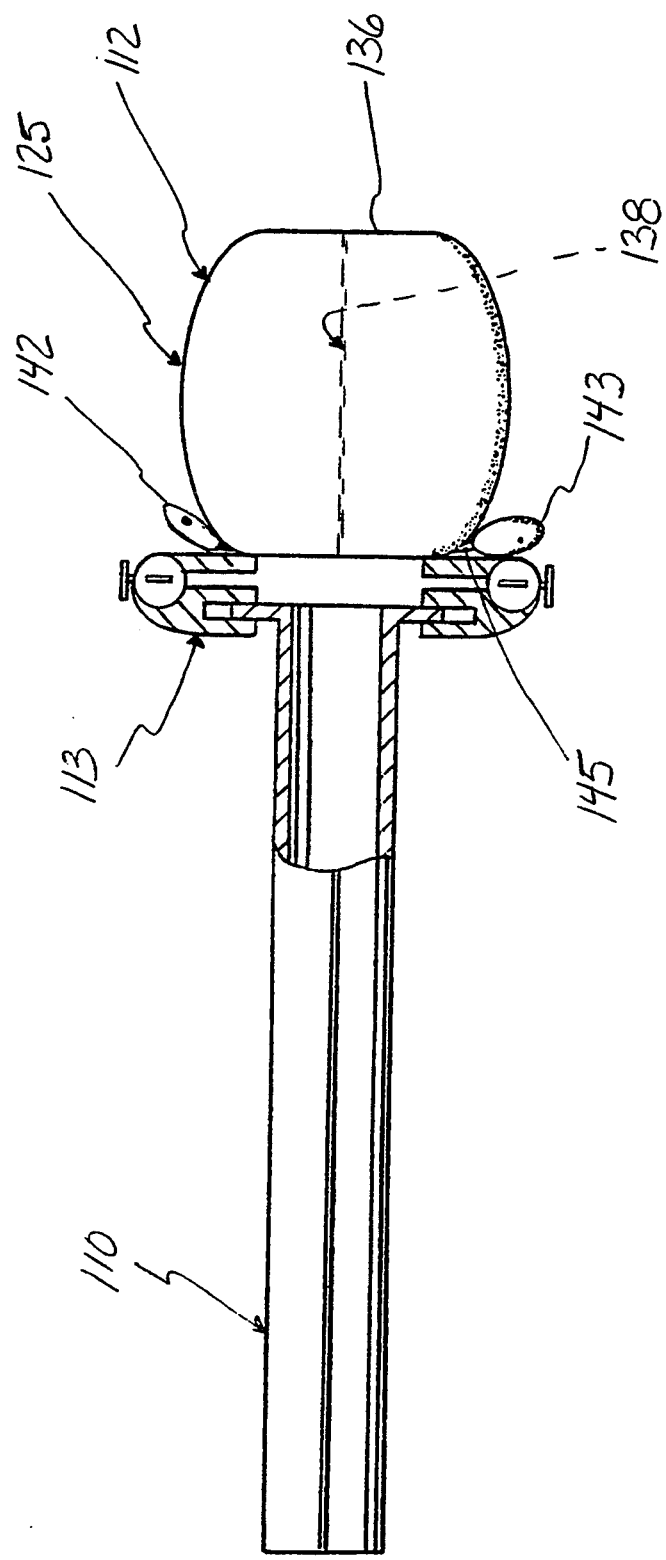
FIG. 2 is a side view, partly in section, of a modification of the endoscopic portal according to the present invention.
Figure 3:
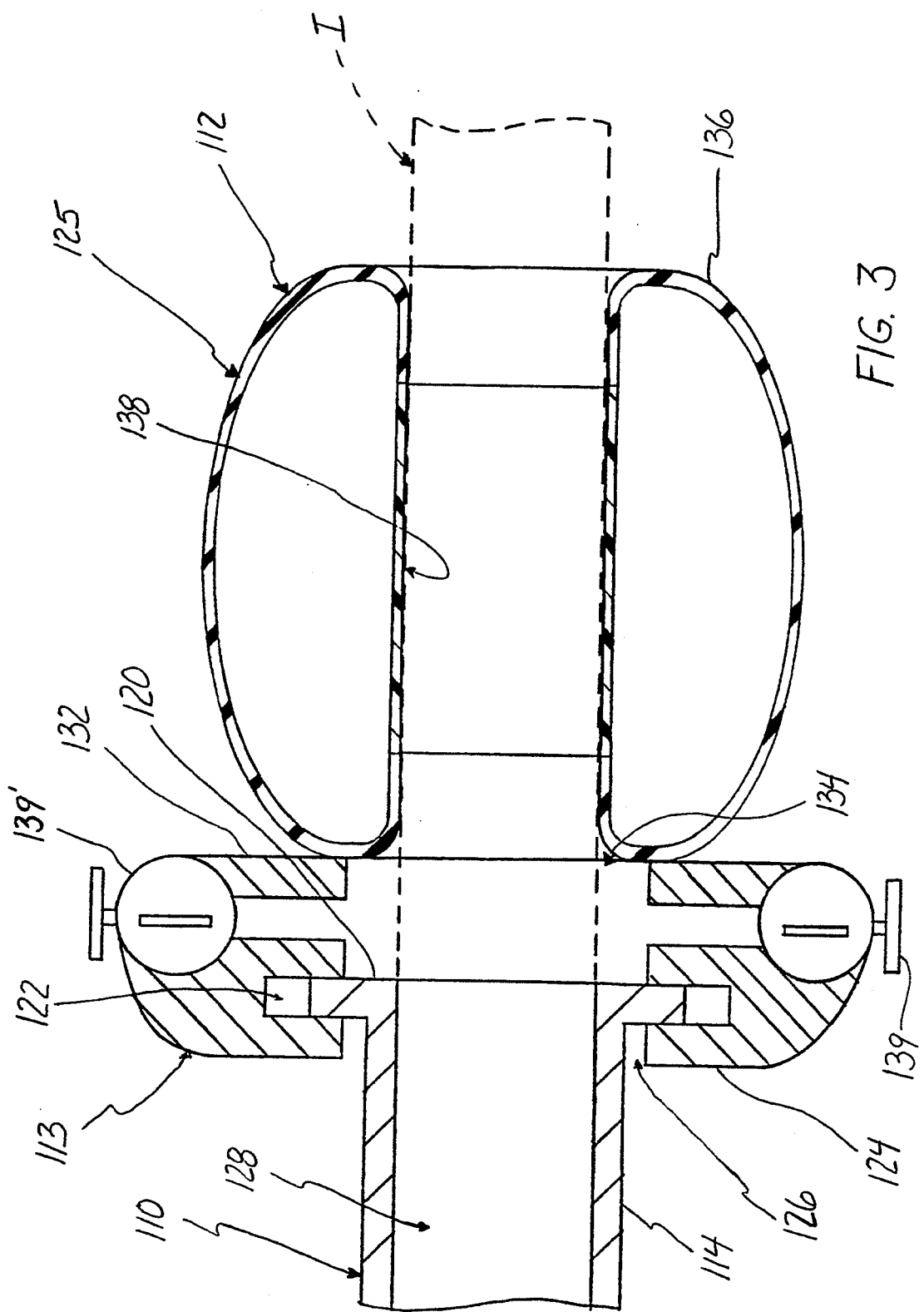
FIG. 3 is an enlarged, sectional view of the valve assembly for the endoscopic portal of FIG. 2.

A modification of the endoscopic portal including a valve assembly according to the present invention is illustrated at 110 and 112, respectively, in FIG. 2. Endoscopic portal 110 and valve assembly 112 are similar to endoscopic portal 10 and valve assembly 12 except that bladder 136 of valve assembly 112 forms a housing 125 for endoscopic portal 110. Valve assembly 112 includes bladder 136 and a hub 113 joined to a forward end of the bladder 136 by any suitable means. Bladder 136 is filled with compressible material, such as air, saline, gel, foam, or sponge or combinations thereof, for example, to have an external configuration in the expanded state to facilitate grasping by a surgeon. In the expanded state, passage 138 through the bladder 136 is closed to seal valve assembly 112 and prevent the flow of fluid therethrough. Bladder 136 can be pre-filled with compressible material to be normally pressurized in the expanded state; and, where air is utilized as the compressible material, various devices, such as valves, can be connected with the bladder to permit selective release of air for controlling the size of the bladder when inserting and removing relatively large objects. If desired, a device can be connected with the bladder 136 to supply air thereto for repressurization or reexpansion thereof. As illustrated in FIG. 2, a squeeze bulb 143 is connected with bladder 136 by a tube 145 for depressurization of the bladder where the bladder is supplied with air, and a squeeze bulb 142 is connected with bladder 136 for supplying air to pressurize the bladder. Where depressurization and repressurization of bladder 136 is not desired, squeeze bulbs 143 and 142 need not be provided as illustrated in FIG. 3. As best shown in FIG. 3, hub 113 includes a forward wall 124 having a recess 122 therein receiving flange 120 of sleeve 114 of endoscopic portal 110 and an aperture 126 allowing passage therethrough by sleeve 114. A rear wall 132 of hub 113 is spaced proximally a minimal distance from forward wall 124 to reduce the length of housing 125, and an annular opening 134 in rear wall 132 aligned with aperture 126 is normally covered or sealed by bladder 136 in the expanded state to prevent fluid flow through valve assembly 112. Stopcocks 139 and 139' communicating with the interior of hub 113 are mounted between the forward and rear walls, the position of the stopcocks being particularly advantageous for bilateral operation. Stopcocks 139 and 139' can be utilized to supply separate fluids to or to aspirate fluids from an anatomical cavity or one of the stopcocks, such as stopcock 139, can be utilized to supply a fluid to the anatomical cavity while the other stopcock 139' can be utilized to aspirate fluid from the anatomical cavity.

Figure 4:
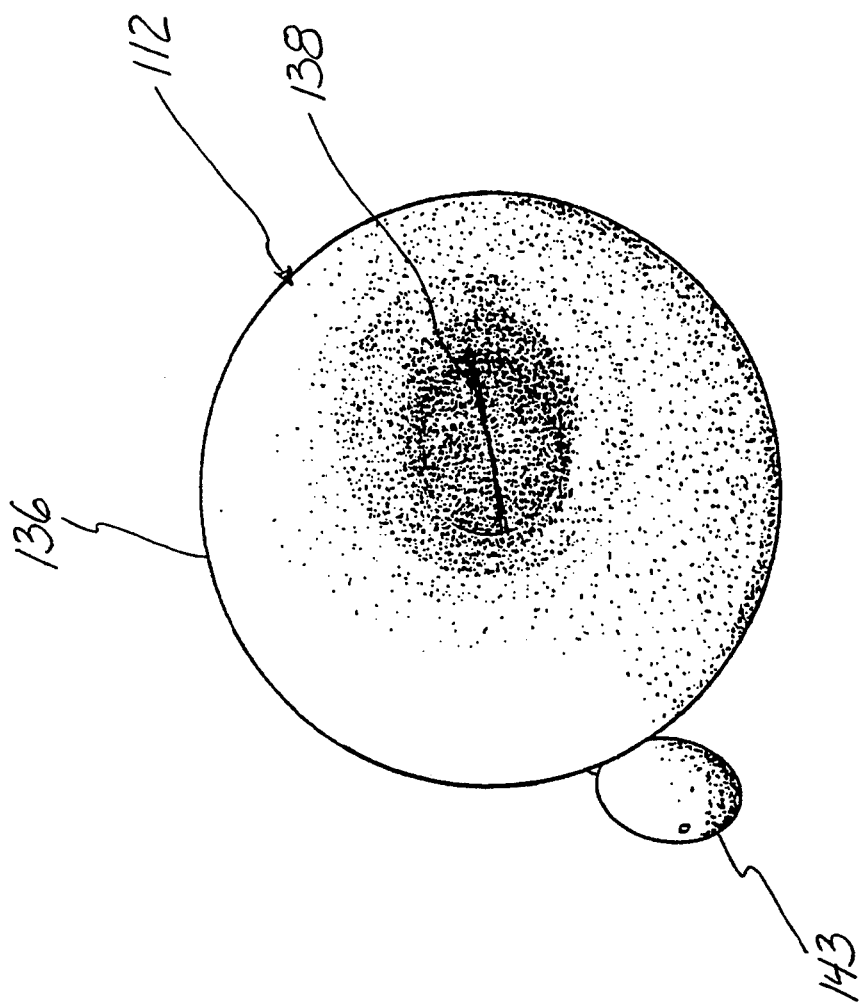
FIG. 4 is a perspective view of the valve assembly of FIG. 3 with a passage of the valve assembly closed.
Figure 5:
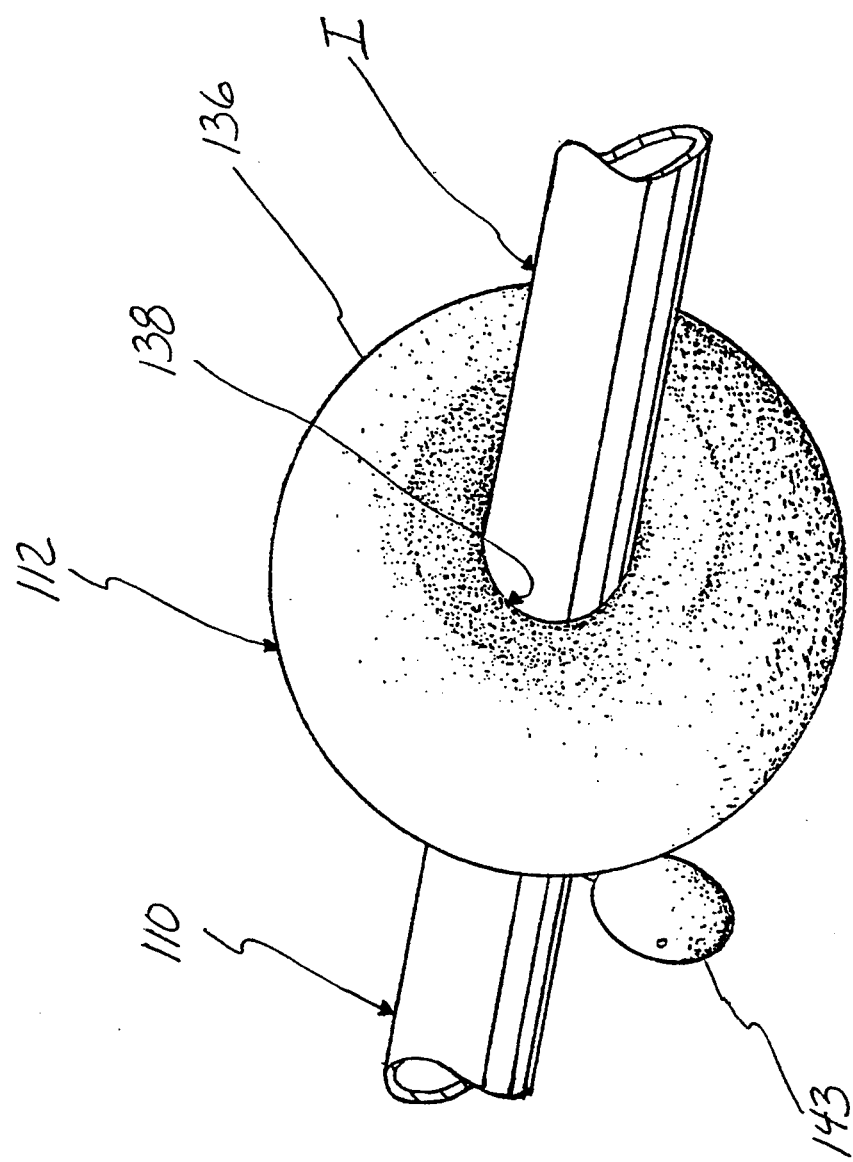
FIG. 5 is a perspective view of the valve assembly of FIG. 4 with the passage open to receive a surgical instrument therethrough.

Operation of endoscopic portal 110 and valve assembly 112 is similar to that described for endoscopic portal 10 and valve assembly 12 in that a penetrating instrument as well as other instruments and objects of various sizes can be inserted in and removed from an anatomical cavity through lumen 128 via the passage 138 of valve assembly 112. Bladder 136 can be normally provided in the expanded state with the bladder filled with compressible material and the passage 138 closed as illustrated in FIG. 4 to form a seal preventing the flow of fluid therethrough. Where air is utilized as the compressible material, the bladder can be provided in the contracted state and inflated during use. Upon insertion of an instrument or object, such as instrument I illustrated in FIGS. 3 and 5, in the passage 138, the material in bladder 136 will be compressed causing passage 138 to open to a size just large enough to receive the instrument I. With the instrument I disposed in passage 138, bladder 136 conforms to the shape of the instrument to form a seal therewith. Upon removal of instrument I from the valve assembly 112, passage 138 closes to form a seal preventing the flow of fluid through the valve assembly. Where air is utilized and squeeze bulb 143 is provided, air can be selectively removed from bladder 136 to control or limit the external size of the bladder to remain suitable for grasping by the surgeon while allowing objects relatively large in size to be inserted or removed through the valve assembly.

Another modification of the endoscopic portal including a valve assembly according to the present invention is illustrated at 210 and 212, respectively, in FIG. 6. Endoscopic portal 210 is similar to endoscopic portal 10 and includes a sleeve 214 having a longitudinal slit 230 with opposing edges 231. Each of the edges 231 is serrated or provided with a plurality of teeth 233 along the length thereof, the teeth 233 being in intermeshing engagement in the closed state to prevent misalignment of sleeve 214. Valve assembly 212 includes a bladder 236 that can be pre-filled with compressible material or supplied with compressible material during use and a spine or tree member 237 disposed in bladder 236. Bladder 236 has a truncated conical or nipple-shaped configuration in the expanded state defining a funnel-shaped recess 263 leading to passage 238 through the bladder. A rearward end of bladder 236 is outwardly flared for being secured to a wall of housing 225 mounting the bladder. Interior passage 238 is longitudinally aligned with an aperture 226 and an opening 234 in forward wall 224 and rearward wall 232, respectively, of housing 225. Spine member 237 can be disposed in bladder 236 to partially fill a single interior compartment of the bladder where the bladder is made up of a single interior compartment, or the spine member can wholly or partially fill one or more than one interior compartment of the bladder where the bladder is made up of more than one interior compartment. As shown in FIG. 6, bladder 236 defines a single interior compartment with spine member 237 partially filling the single interior compartment of the bladder. Spine member 237 has a truncated conical or nipple-shaped external configuration with an outwardly flared rearward end corresponding to the configuration of bladder 236. The rearward end of spine member 237 can be made integrally, unitarily with or separate from a forward end of the spine member and can be made of the same material as the forward end or of a different material. The spine member 237 can be secured to a portion of housing 225; and, as shown in FIG. 6, the outwardly flared rearward end of the spine member is secured to the wall of housing 225 mounting bladder 236. To facilitate securement of the spine member 237 to housing 225, at least the portion of the spine member to be secured to the housing can be made of a rigid, substantially rigid or semi-rigid material. As illustrated in FIG. 6, spine member 237 is unitarily, integrally formed in its entirety of a compressible solid material, such as a sponge material. Spine member 237 can have various configurations and structure and can be made in many various ways to guide or bias the bladder to compress passage 238 and to permit opening of the valve assembly upon application of external pressure along the passage. For example, spine member 237 can be made of a compressible solid material as shown, a compressible fluid or a spring or other mechanical bias device such as spring arms and coil springs to guide the bladder to close the passage. Depending on the configuration and arrangement for spine member 237, bladder 236 can be guided to compress passage 238 in the non-expanded state to normally seal the valve assembly 212 without expansion of the bladder such that the bladder can be utilized with the spine member alone to close the passage and form a seal with objects therein. Bladder 236 is designed to be filled with air during use, and squeeze bulbs 242 and 243 are mounted externally along housing 225 to communicate with the interior of bladder 236 for supplying air to and removing air from the bladder, respectively.

Operation of endoscopic portal 210 and valve assembly 212 is similar to that previously described. Bladder 236 can normally be provided in the contracted state with spine member 237 guiding the bladder to close passage 238. Objects can be inserted and removed through passage 238 with the taper of recess 263 leading to passage 238 facilitating the insertion of instruments or objects. Depending on the size of the objects to be disposed in passage 238, the spine member 237 may be sufficient to cause bladder 236 to sealingly contact the objects without requiring expansion of the bladder. Where the objects to be inserted or removed are too small to be adequately sealed by the spine member 237 or where increased sealing force is desired, bladder 236 can be inflated to the expanded state with squeeze bulb 242. Upon removal of objects from the valve assembly 212, spine member 237 will guide bladder 236 to close passage 238 and thusly seal the valve assembly.

A modification of a valve assembly for use with the endoscopic portal according to the present invention is illustrated at 312 in FIG. 7. Valve assembly 312 includes a bladder 336 having a truncated conical configuration in the expanded state and joined at a rearward end thereof to an end flange 347. End flange 347 can have an annular configuration and can be made of a rigid, substantially rigid or semi-rigid material to facilitate mounting of the valve assembly within a housing or use of the valve assembly itself as a housing. End flange 347 has an opening 334 therein sufficiently large in size to receive various sizes of instruments or objects to be inserted or removed through the valve assembly. Bladder 336 is filled with a compressible material; and, as shown in FIG. 7, bladder 336 is filled with a sponge material. A spine member 337 is disposed in bladder 336 to guide the bladder to close a passage 338 therethrough aligned with opening 334. Spine member 337 is made up of a plurality of spring arms 349 joined at their ends to end flange 345 and arranged around opening 334. The spring arms 349 are biased inwardly toward passage 338 to guide bladder 336 to close the passage and are movable in a direction outwardly of the passage by objects inserted or removed therethrough. An external compressing device including one or more bands 351 of stretchable material, such as elastic or rubber, are disposed externally around bladder 336 to further bias the bladder to close or compress passage 338 while permitting the external size of the bladder to be expanded when objects are inserted or removed through the passage.

Operation of valve assembly 312 is similar to that previously described in that the valve assembly is normally provided in the expanded state with spine member 337 and external compressing devices 351 guiding bladder 336 to close passage 338. Upon insertion of an object in passage 338, the passage will be opened due to the external force applied by the object causing the material in bladder 336 to be compressed and spring arms 349 to be moved in a direction outwardly of the passage. With an object disposed in passage 338, inwardly directed force applied by spring arms 349 as well as compressive force applied by compressing devices 351 in the direction of the passage enhances the seal formed by bladder 336 with the object. It will be appreciated that bladder 336 need not be supplied with compressible material and that the spine member 337 alone can be utilized with the bladder to compress passage 338 while allowing opening of the passage to receive objects therein in sealing relation with the bladder.

An additional modification of an endoscopic portal including a valve assembly according to the present invention is illustrated at 410 and 412, respectively, in FIG. 8. Endoscopic portal 410 includes a sleeve 414 having a proximal end 418 joined to bladder 436 of valve assembly 412 with lumen 428 of the sleeve communicating with the interior of the bladder. Sleeve 414 passes through an opening in a hub 413 having a stopcock 439 communicating with a channel 457 in the hub, the channel communicating with lumen 428. Valve assembly 412 forms a housing 425 for endoscopic portal 410 and includes bladder 436 defining a passage 438 therethrough aligned with lumen 428 and an opening 434 in an end wall 459 joined to a rearward end of the bladder. Bladder 436 includes one or a plurality of inner walls, partitions or membranes 461, and the membranes 461 can be arranged in many various ways including angularly, radially and transverse to passage 438. As shown in FIG. 8, bladder 436 includes an inner membrane 461 tapering in a distal direction from end wall 459 to passage 438 to define a funnel-shaped recess 463 leading to passage 438. Bladder 436 is filled with compressible material to normally be in an expanded state; and, as shown in FIG. 8, the interior of bladder 436 except for recess 463 is filled with a gel material. Bladder 436 can have various external configurations in the expanded state; and, as shown, the bladder has a cylindrical external configuration. End wall 459 can have various configurations in accordance with the configuration of bladder 436, the end wall 459 being circular.

Operation of endoscopic portal 410 and valve assembly 412 is similar to that previously described in that valve assembly 412 is normally provided in the expanded state to close passage 438 and define a cylindrical housing 425 for being grasped by a surgeon. The tapered configuration of recess 463 facilitates insertion of objects in passage 438 via opening 434 with the passage opening to receive such objects in sealing relation with the bladder. Fluid can be supplied to or removed from an anatomical cavity via stopcock 439.

A further modification of a valve assembly for use with the endoscopic portal according to the present invention is illustrated at 512 in FIG. 9, valve assembly 512 being particularly advantageous in reducing the force required to open the passage of the valve assembly without requiring material to be removed from the bladder. Valve assembly 512 includes a bladder 536 for being supplied with compressible material and having a plurality of concentrically arranged membranes or partitions 561 disposed around passage 538 to define a plurality of concentric compartments. Compressible material is supplied between the membranes 561 to fill the compartments.

According to a method of operation for valve assembly 512, the valve assembly is normally provided in an expanded state with the compartments filled with compressible material to cause bladder 536 to close passage 538. Upon insertion of an object in passage 538, the passage will be opened incrementally beginning with compression of material within the innermost compartment such that the force required to open the passage to receive the object is reduced.

Figure 10:
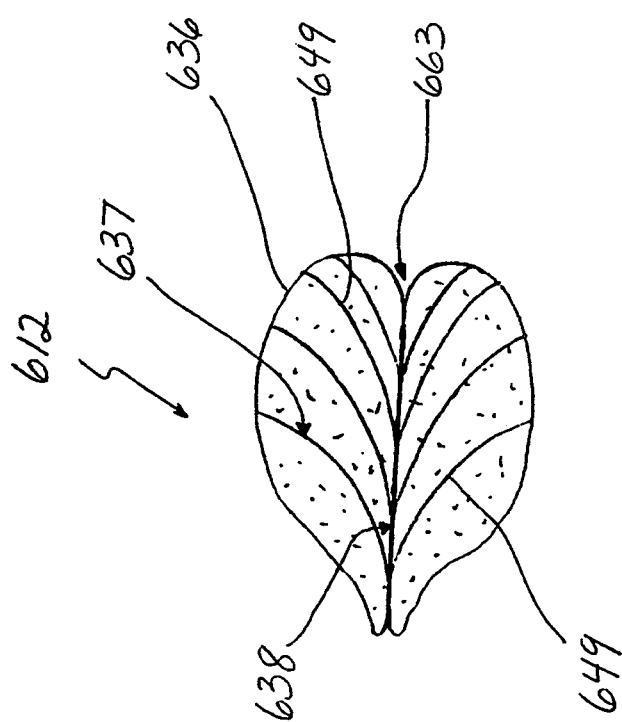
FIG. 10 is a sectional view of another modification of the valve assembly for the endoscopic portal according to the present invention.

A further modification of a valve assembly for use with the endoscopic portal according to the present invention is illustrated at 612 in FIG. 10. Valve assembly 612 includes a bladder 636 having a heart-shaped configuration in the expanded state defining a tapered recess 663 at a rearward end of the valve assembly to facilitate insertion of instruments in passage 638. A spine member 637 is disposed in bladder 636 and includes a plurality of curved spring arms 649. Spring arms 649 are pivotally connected at their ends along the internal surface of an outer portion of the bladder 636 and curve inwardly in a distal or forward direction toward passage 638 to contact the inner portion of the bladder defining the passage. Spring arms 649 bias bladder 636 to normally assume the heart-shaped configuration shown with passage 638 closed or compressed to form a seal through the valve assembly. By providing a sufficient number and arrangement of spring arms, the spine member 637 alone can be used to maintain the external configuration of the bladder and compress passage 638 while allowing the passage to be opened by an object inserted therein; however, if desired, the bladder can be filled with a compressible material, such as foam as illustrated in FIG. 10.

In use, valve assembly 612 is normally provided in the expanded state with recess 663 being tapered to passage 638 for ease of insertion of instruments. In the expanded state, passage 638 is compressed due to the bias of spring arms 649 and the pressure of the compressible material where the bladder is supplied with a compressible material. Upon insertion of an instrument or other object in passage 638 via recess 663, the passage will be opened due to the external force of the instrument causing spring arms 649 to be deflected outwardly. With the instrument disposed in passage 638, spring arms 649 will be biased toward the instrument causing the passage to be compressed around the instrument and the bladder 636 to sealingly contact the instrument.

Figure 11:
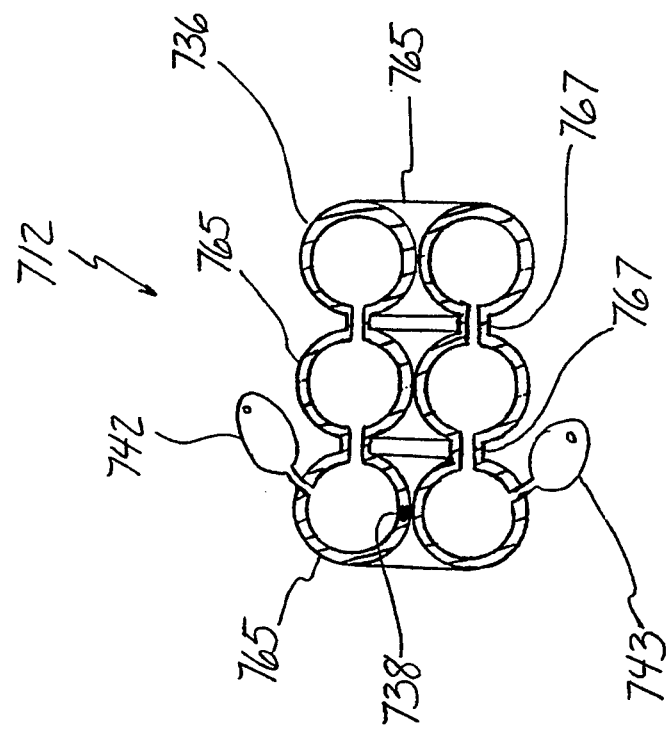
FIG. 11 is a sectional view of an additional modification of the valve assembly for the endoscopic portal according to the present invention.

An additional modification of a valve assembly for use with the endoscopic portals according to the present invention is illustrated at 712 in FIG. 11. Valve assembly 712 includes a bladder 736 made up of one or a plurality of tubular members 765. As shown in FIG. 11, valve assembly 712 includes a plurality of tubular members 765 molded as one-piece, the tubular members being donut-shaped in configuration and longitudinally aligned with one another to define a passage 738 through the valve assembly. Tubular members 765 are interconnected by channels 767, and squeeze bulbs 742 and 743 communicate with the interior of bladder 736 for supplying air to and removing air from the bladder, respectively. If desired, tubular members 765 can be separate from one another and not interconnected, and separate devices can be provided for supplying air to and removing air from the tubular members. It will be appreciated that the one or more tubular members can be arranged in many various ways to form the valve assembly. For example, a valve assembly 812 illustrated in FIG. 12 has a bladder 836 formed by rolling, wrapping, winding or coiling a length of tubing 865 a plurality of times to define a passage 838 through the valve assembly as shown in FIG. 12. The tubing 865 can be wound or coiled in many various ways to form a spiral or helical coil, for example, and the tubing can be wrapped to form a single layer as shown or multiple layers.

Operation of valve assembly 712 is similar to that previously described in that bladder 736 is supplied with compressible material to compress passage 738 and close the valve assembly. The passage 738 can be opened to receive instruments therethrough with the compressible material compressing the passage around the instruments to cause the bladder 736 to sealingly contact the instruments.

With the valve assemblies of the present invention, a single passage for receiving instruments and objects through the valve assemblies can be opened to various sizes corresponding to the sizes of instruments and objects passing therethrough in sealing relation with the valve assemblies. By providing the passage to be normally closed and to be compressed around instruments passing therethrough, fluid flow through the valve assemblies is prevented prior to insertion of, during insertion of and upon removal of instruments. The valve assemblies can be normally provided in a contracted or non-expanded state or in an expanded state and can be used with a housing or without or in place of a housing. By utilizing the valve assemblies without or in place of a housing, the endoscopic portals can be inexpensively manufactured to be disposable for single patient use. By controlling the external size of the valve assemblies via removal of compressible material, limitations on the size of objects that can be inserted and removed through the endoscopic portals as exists with rigid housings can be eliminated. Via selective removal of compressible material, relatively large objects can be inserted or removed from the valve assemblies while minimizing the external size thereof to facilitate grasping by the surgeon where the valve assembly forms the housing or for minimizing the size of a housing where the valve assembly is mounted in a housing. The valve assemblies can be utilized with compressible material alone, a spine member alone, an external passage compressing device or combinations thereof to compress the passages of the valve assemblies. The passage of the valve assemblies can be caused to conform to the size and shape of instruments passing therethrough, such that more than one instrument can be passed simultaneously through the valve assemblies as well as irregularly shaped instruments and objects. By utilizing an external compressing device, the valve assemblies can be biased or guided to close the passage while increasing the sealing force of the valve assemblies on objects in the passage. The force required to open the passages of the valve assemblies can be reduced with use of a plurality of concentrically arranged membranes providing incremental opening of the passage. By providing an expandable endoscopic portal, the present invention permits instruments and objects larger than the diameter of the lumen of the portal to be inserted in and removed from an anatomical cavity.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An endoscopic portal for establishing communication with an anatomical cavity through a wall of the cavity comprising;
   an elongate tubular portal sleeve for insertion through the cavity wall and having an open distal end for positioning within the cavity and an open proximal end for positioning externally of the cavity; and
   a valve assembly disposed adjacent said portal sleeve proximal end and including a bladder having a passage therethrough for permitting insertion of instruments of various sizes in said portal sleeve through said passage and means in said bladder for compressing said passage to cause said bladder to sealingly contact instruments inserted through said passage.

2. An endoscopic portal as recited in claim 1 wherein said passage includes a longitudinal axis and said means for compressing includes means for compressing said passage in a direction transverse to said axis.

3. An endoscopic portal as recited in claim 2 wherein said means for compressing includes a spine member in said bladder for biasing said bladder to sealingly contact the instruments.

4. An endoscopic portal as recited in claim 2 wherein said means for compressing includes a compressible material in said bladder.

5. An endoscopic portal as recited in claim 3 wherein said spine member is made of a compressible material.

6. An endoscopic portal as recited in claim 3 wherein said spine member includes a spring.

7. An endoscopic portal as recited in claim 4 wherein said compressible material includes a compressible fluid.

8. An endoscopic portal as recited in claim 4 wherein said compressible material includes a solid compressible material.

9. An endoscopic portal as recited in claim 4 and further including means disposed externally around said bladder for biasing said bladder to compress said passage.

10. An endoscopic portal as recited in claim 4 and further including a spine member in said bladder for guiding said bladder to compress said passage.

11. An endoscopic portal as recited in claim 4 and further including means connected with said bladder for supplying said bladder with said compressible material.

12. An endoscopic portal as recited in claim 4 wherein said bladder includes a portion defining said passage and at least said passage defining portion of said bladder is made of an expandable, tearing-resistant materials.

13. An endoscopic portal as recited in claim 4 wherein said bladder includes a portion defining said passage and said passage defining portion is made up of a plurality of concentrically arranged membranes of expandable material.

14. An endoscopic portal as recited in claim 9 wherein said external biasing means includes at least one band of stretchable material disposed around said bladder.

15. An endoscopic portal as recited in claim 10 wherein said spine member is made of a compressible material.

16. An endoscopic portal as recited in claim 10 wherein said spine member includes a spring.

17. An endoscopic portal as recited in claim 11 wherein said compressible material includes air and said means for supplying includes a squeeze bulb.

18. An endoscopic portal as recited in claim 13 wherein a normally close said passage and to permit said passage to be opened incrementally in the direction transverse to said axis upon insertion of the instruments therethrough.

19. An endoscopic portal as recited in claim 16 wherein said spring includes a plurality of spring arms biased to compress said passage.

20. An endoscopic portal for establishing communication with an anatomical cavity through a wall of the cavity comprising;
   an elongate tubular portal sleeve for being inserted through the cavity wall and having an open distal end for being positioned within the cavity and an open proximal end for being positioned externally of the cavity; and
   a valve assembly disposed adjacent said portal sleeve proximal end and including a bladder having a passage therethrough permitting instruments of various sizes to be inserted through said valve assembly, said bladder being filled with a compressible material to cause said passage to conform to the size of the instruments inserted through said valve assembly to prevent passage of fluid through said valve assembly.

21. An endoscopic portal as recited in claim 20 and further including means for removing at least some of said material from said bladder.

22. An endoscopic portal as recited in claim 20 Wherein said bladder has a configuration when filled with said material for being grasped by a surgeon.

23. An endoscopic portal as recited in claim 20 and further including a housing mounting said portal sleeve proximal end and wherein said bladder is disposed in said housing.

24. An endoscopic portal as recited in claim 20 wherein said bladder has a toroidal external configuration when filled with said material.

25. An endoscopic portal as recited in claim 20 wherein said bladder has a nipple-shaped external configuration wren filled with said material.

26. An endoscopic portal as recited in claim 20 wherein said bladder has an external configuration when filled with said material to normally close said passage and said external configuration defines a recess tapering to said passage when closed to facilitate, insertion of instruments through said valve assembly.

27. An endoscopic portal as recited in claim 26 wherein said bladder has a heart-shaped external configuration when filled with said material.

28. An endoscopic portal as recited in claim 20 wherein said bladder is made up of a length of spirally wound tubing.

29. An endoscopic portal as recited in claim 20 wherein said portal sleeve has a longitudinal axis and a lumen therethrough expandable in a direction transverse to said axis.

30. A method of inserting an instrument through an endoscopic portal passing through a wall of an anatomical cavity including the steps of;
   inserting an instrument through a passage of a bladder filled with compressible material adjacent a proximal end of the endoscopic portal disposed externally of the anatomical cavity; and
   compressing the passage with the compressible material to cause the bladder to contact the instrument in sealing relation.

* * * * *